US012718677B2

(12) United States Patent
Bistany et al.

(10) Patent No.: US 12,718,677 B2
(45) Date of Patent: Aug. 25, 2026

(54) SYSTEM AND METHOD FOR AIR QUALITY MONITORING AND REPORTING

(71) Applicant: ZEPTIVE, INC, Andover, MA (US)

(72) Inventors: Loucinda C. Bistany, Methuen, MA (US); William D. Hargett, Chelmsford, MA (US); Stephen S. Milt, Winchester, MA (US)

( * ) Notice: Subject to any disclaimer, the term of this patent is extended or adjusted under 35 U.S.C. 154(b) by 147 days.

(21) Appl. No.: 18/123,274

(22) Filed: Mar. 18, 2023

(65) Prior Publication Data

US 2023/0298451 A1 Sep. 21, 2023

Related U.S. Application Data

(60) Provisional application No. 63/321,526, filed on Mar. 18, 2022.

(51) Int. Cl.
*F24F 11/64* (2018.01)
*G01N 15/06* (2006.01)
(Continued)

(52) U.S. Cl.
CPC ............. *G08B 21/12* (2013.01); *G01N 15/06* (2013.01); *G01N 33/0063* (2013.01);
(Continued)

(58) Field of Classification Search
CPC ........ G07C 5/008; G07C 5/08; G07C 5/0866; E05Y 2400/42; E05Y 2900/55; E05F 15/695; E05F 15/70; E05F 15/71; B60H 1/00771; B60H 1/008; B60H 2003/0683; B60H 3/0608; Y02B 30/70; Y02A 50/20; G01N 33/004; G01N 1/2273; G01N 1/24; G01N 1/26; G01N 33/0009; G01N 33/0031; G01N 33/0037; G01N 33/0039; G01N 33/0042; G01N 33/0044; G01N 33/0063; G01N 15/06; G01N 2015/0046; G01N 33/0004; G01N 33/0067; F24F 11/30; F24F 11/74; F24F 1/0071; F24F 1/0073; F24F 1/0076; F24F 11/46; F24F 11/52; F24F 11/56; F24F 11/61; F24F 11/63; F24F 11/76; F24F 11/77; F24F 11/88;
(Continued)

(56) References Cited

U.S. PATENT DOCUMENTS 9,449,491 B2 * 9/2016 Sager .................. G06F 3/04842
12,068,076 B1 * 8/2024 Alexopoulos .......... G16H 40/20
(Continued)

*Primary Examiner* — Dionne Pendleton

(57) ABSTRACT

A personal air quality detection device is configured to monitor the air quality of a user based on the location of the personal air quality detection device. To this end, the personal air quality detection device first determines a location of the user. Based on the determined location, the personal air quality detection device selects a location profile associated with the determined location indicating one or more substance threshold values. Using a substance threshold value indicated by the location profile, the personal air quality detection device monitors the location for a substance of interest by comparing a measurement of the substance of interest to the substance threshold value. Based on the comparison, the personal air quality detection device displays one or more notifications associated with the substance of interest.

18 Claims, 6 Drawing Sheets

(51) Int. Cl.
*G01N 33/00* (2006.01)
*G08B 5/36* (2006.01)
*G08B 21/12* (2006.01)
*G08B 21/18* (2006.01)

(52) U.S. Cl.
CPC .......... *G01N 33/0067* (2013.01); *G08B 5/36* (2013.01); *G08B 21/182* (2013.01)

(58) Field of Classification Search
CPC .............. F24F 11/89; F24F 2011/0006; F24F 2110/10; F24F 2110/50; F24F 2110/70; F24F 2120/00; F24F 8/192; F24F 8/22; F24F 8/30; A61B 1/00006; A61B 1/000094; A61B 1/000096; A61B 1/00042; A61B 1/0005; A61B 1/0052; A61B 1/051; A61B 1/0661; A61B 1/0684; A61B 17/068; A61B 18/00; A61B 18/1206; A61B 18/14; A61B 18/1442; A61B 18/1445; A61B 2017/00022; A61B 2017/00044; A61B 2017/00061; A61B 2017/00106; A61B 2017/00115; A61B 2017/00119; A61B 2017/00442; A61B 2017/07271; A61B 2018/00642; A61B 2018/00684; A61B 2018/00744; A61B 2018/00863; A61B 2018/00994; A61B 2018/167; A61B 2034/2065; A61B 2034/254; A61B 2034/256; A61B 2090/061; A61B 2090/365; A61B 2218/002; A61B 2218/007; A61B 2218/008; A61B 2505/05; A61B 34/25; A61B 34/37; A61B 5/0035; A61B 5/0071; A61B 5/02042; A61B 5/021; A61B 5/026; A61B 5/318; A61B 5/4821; A61B 5/7264; A61B 90/361; A61B 90/98; B60K 2360/592; B60K 35/10; B60K 35/22; B60K 35/28; B60K 35/85; B60R 16/0237; B60W 2050/143; B60W 2050/146; B60W 2540/221; B60W 2555/20; B60W 2556/45; B60W 2556/50; B60W 50/14; G01K 1/14; G05B 15/02; G05B 2219/2642; G06F 3/04842; G06F 3/0485; G06T 2207/10068; G06T 7/20; G06T 7/70; G06V 2201/034; G08B 13/19682; G08B 13/19684; G08B 13/19695; G08B 19/005; G08B 21/0208; G08B 21/12; G08B 21/182; G08B 23/00; G08B 25/00; G08B 25/001; G08B 25/002; G08B 25/003; G08B 25/005; G08B 25/006; G08B 25/008; G08B 25/10; G08B 27/001; G08B 27/006; G08B 29/188; G08B 5/36; H04W 12/06; H04Q 2209/823; H04Q 9/00; H04N 7/181; H04N 7/183; H04N 7/188; H04L 12/2825; H04L 12/2827; H04L 2012/2841; H04L 41/0803; H04L 63/083; H04L 67/125; G16H 20/40; G16H 30/20; G16H 30/40; G16H 40/60; G16H 40/63; G16H 40/67; G16H 50/20; G08C 17/02; G08C 19/00
See application file for complete search history.

(56) References Cited

U.S. PATENT DOCUMENTS

| | | | | |
|---|---|---|---|---|
| 2009/0112525 | A1* | 4/2009 | Adani | G08B 17/00 702/189 |
| 2015/0278456 | A1* | 10/2015 | Bermudez Rodriguez | G16H 40/20 705/2 |
| 2016/0211985 | A1* | 7/2016 | Castillo | F24F 11/62 |
| 2018/0264160 | A1* | 9/2018 | Benedek | A61L 2/10 |
| 2022/0304529 | A1* | 9/2022 | Jones | A47L 9/28 |
| 2025/0189157 | A1* | 6/2025 | Goldenson | G08B 21/14 |

* cited by examiner

SYSTEM AND METHOD FOR AIR QUALITY MONITORING AND REPORTING

FIELD OF INVENTION

The present invention relates generally to air quality monitoring and reporting. In particular, the present invention is directed to systems and methods for personalized air quality monitoring and reporting air quality data using one or more personal air quality detection devices.

BACKGROUND

Air quality detection systems are used in environments to monitor and detect potentially dangerous or harmful airborne substances. However, such systems are stationary and take a one-size-fits-all approach to air quality monitoring which does not allow for air quality monitoring to be based on the needs of specific users. As such, substances that are potentially harmful to certain users may not be monitored or reported by these systems and a user may be exposed to potentially harmful substances. Further, though wearable technology systems exist that measure metrics of one or more users and their environments, such wearable technology systems are not configured to monitor air quality or personalize such monitoring based on a user's needs.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings.

DETAILED DESCRIPTION

Systems and techniques described herein are directed to detecting and reporting personal air quality for one or more users. For example, a personal air quality system includes one or more personal air quality detection devices configured to detect and report the presence of one or more aerosolized substances in one or more environments proximate to one or more users. To this end, in some embodiments, a personal air quality device system includes one or more particle sensors each configured to monitor a portion of an environment proximate to a user for one or more aerosolized substances. "Proximate to a user," as used herein, includes within a radial distance from a center point within which one or more air quality metrics (e.g., particle count, humidity, particle composition) can be measured by one or more sensors. That is to say, within an environment having a size in which the air quality is measurable by one or more sensors. The system further compares the monitored air quality metrics to substance threshold values based on one or personal metrics associated with the user. Such personal metrics include, for example, occupation, conditions (e.g., asthma, chronic obstructive pulmonary disease (COPD), emphysema, cystic fibrosis, allergies), user preferences (e.g., tolerance for substances, sensitivity to substances, range, power settings). Based on the comparison, the system generates one or more notifications, alerts, or both that are delivered to the user.

Figure 1:
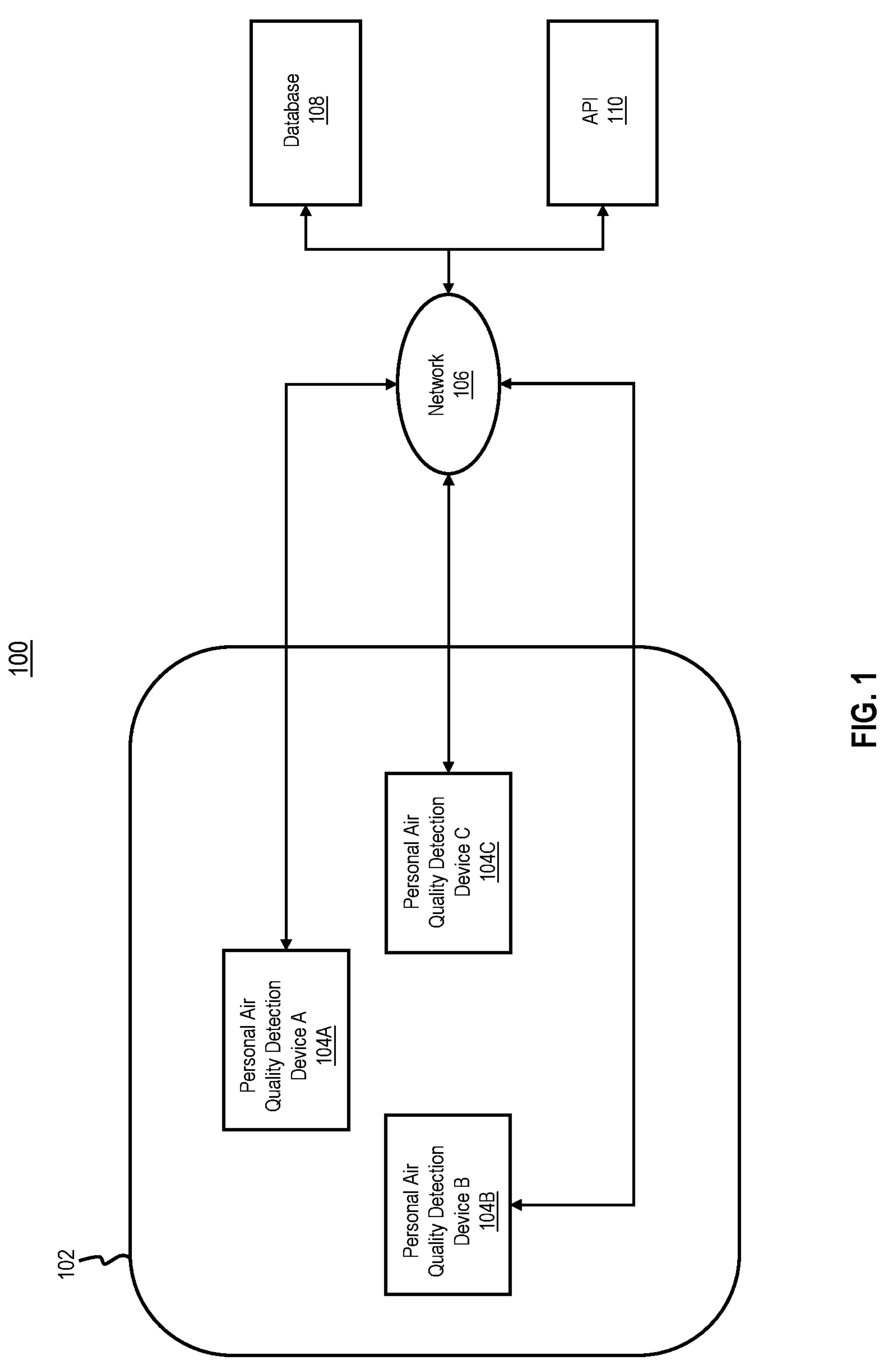
FIG. 1 illustrates a block diagram of a personal air quality detection system, according to embodiments.

Referring now to FIG. 1, personal air quality detection system 100 for air quality detection and notification is illustrated. According to embodiments, personal air quality detection system 100 is configured to notify one or more users of the detection of substances of interest including, but not limited to, aerosolized particles proximate to the one or more users. To this end, personal air quality detection system 100 includes one or more personal air quality detection devices 104 each associated with one or more users and configured to monitor for substances of interest in a first portion of an environment 102 (e.g., a school, an office building, a residence, a dormitory, a warehouse, a factory, a laboratory, a hospital, yard, outdoor area). These personal air quality detection devices 104 are each configured to detect the presence of one or more substances of interest that include, for example, one or more airborne gasses, and/or particles that are to be monitored in at least a portion of an environment. In embodiments, substances of interest can include substances that are illegal, prohibited, or discouraged for one or more users associated with one or more personal air quality devices 104, for example, emissions from a vaporization device (e.g., nicotine vaping device, cannabinoid vaping device, tetrahydrocannabinol vaping device), emissions from nicotine products (e.g., cigarettes, cigars, pipes), emissions from illegal, prohibited, or discouraged drugs (e.g., methamphetamine, fentanyl), or any combination thereof. As another example, substances of interest include one or more substances that are hazardous to one or more users associated with one or more personal air quality devices, for example, hazardous gasses (e.g., arsine, dimethyl sulfate, toluene, hydrogen azide, hydrogen cyanide, nitrogen dioxide, ammonia), biological substances (e.g., viruses, bacteria, fungus, pollen, dust, mold), or any combination thereof. As yet another example, substances of interest can include substances not tolerated by one or more users associated with one or more personal air quality detection devices 104, for example, animal odors (e.g., animal urine, animal feces, animal sweat), chemical odors (e.g., perfumes, colognes, body sprays), food odors, or any combination thereof. In embodiments, substances of interest include aerosolized particles, droplets, gasses, or any combination thereof. A portion of an environment 102 includes, for example, any portion of a room, floor, level, wing, or building of an environment. As an example, a portion of the environment 102 includes a hallway of a floor of an environment 102. According to some embodiments, personal air quality detection system 100 is configured to measure the air quality of one or more portions of the environment 102 proximate to a user. For example, air quality detection system 100 is configured to measure the air quality within a radial distance from a center point (e.g., the user, a personal air quality detection device 104, or both).

According to embodiments, each personal air quality device 104 is associated with one or more users. For example, a personal air quality device 104 is associated with one or more user profiles, personal metrics, user credentials (e.g., usernames, passwords), or any combination thereof associated with one or more users. In some embodiments, each personal air quality device 104 is associated with a respective user, while in other embodiments two or more air quality devices 104 are associated with the same user. Such user profiles, for example, are each associated with a respective user of a personal air quality device 104 and include data identifying one or more substances of interest to be measured (e.g., data identifying which substances of interest to monitor in a portion of an environment 102), one or more threshold values (e.g., substance threshold values) associated with one or more substances of interest, one or more personal metrics of a user, or any combination thereof. As an example, a user profile includes data indicating one or more one or more substances of interest to be measured that are to harmful and to be avoided by a user. In embodiments, personal metrics, for example, include one or more conditions (e.g., allergies to substances of interest, illnesses, diagnoses, intolerances to substances of interest, sensitivities to substances of interest), measurements (e.g., $VO_2$ max, heartrate, heart rate recovery, historical measurements), identifying information (e.g., occupation, age, sex, gender), preferences (e.g., aversions to substances of interest, tolerances of substances of interest, power preferences for a personal air quality device 104, timing preferences for a personal air quality device 104), or any combination thereof of a user of a personal air quality device 104.

In embodiments, one or more personal air quality devices 104 include or are otherwise disposed within (e.g., embedded, encased in, or enclosed within) a wearable object. Such wearable objects include, for example, watches, bracelets, rings, pins, clips, or the like that are attachable to, wearable by, or disposable on a user by way of, for example, mechanical connection to the clothing, body, hair, joints, of the user, graspable by the user, implanted in the body of the user, or any combination thereof. According to embodiments, one or more personal air quality devices 104 include or are otherwise disposed within (e.g., embedded, encased in, or enclosed within) a wearable technology device. A wearable technology device includes, for example, any hardware-based circuitry, software-based circuitry or both of an electronic device that is attachable to, wearable by, or disposable on a user by way of, for example, mechanical connection to the clothing, body, hair, joints, of the user, graspable by the user, implanted in the body of the user, or any combination thereof. In embodiments, a wearable technology device includes, for example, location services, global positioning system (GPS) services, environmental sensors, weather sensors, WI-FI, wireless network capability, or any combination thereof, to name a few. As an example, a wearable technology device includes, but is not limited to a compute-enabled watch (e.g., a smartwatch), wearable sensor, compute-enabled band (e.g., a fitness tracker), compute-enabled ring (e.g., smart ring), or the like. Though the example embodiment of FIG. 1 presents personal air quality detection system 100 as having three personal air quality devices (104A, 104B, 104C), in other embodiments, personal air quality detection system 100 can have any number of personal air quality devices 104 each associated with one or more users.

According to embodiments, each personal air quality device 104 includes a sensor suite that includes, for example, one or more particle sensors, chemical sensors, temperature sensors, humidity sensors, or any combination thereof. In embodiments, each personal air quality device 104 comprises or otherwise includes a "detection unit" as disclosed in commonly owned U.S. Pat. No. 11,195,406 entitled "System and method for detection of vaporized aerosols" and filed on Aug. 25, 2020, or U.S. Pat. No. 11,030,877 entitled "Vaporized Aerosol Detection Network" and filed Oct. 16, 2020, both of which are incorporated by reference in their entirety herein. In embodiments, one or more personal air quality devices 104 include one or more particle sensors. Each particle sensor is configured (i.e., calibrated) to detect the presence of one or more predetermined substances of interest proximate to the particle sensor. That is to say, one or more personal air quality devices 104 includes one or more particle sensors configured to monitor the portion of the environment 102 proximate to the personal air quality devices 104, for example, a room, hallway, or portion of a warehouse. According to embodiments, each particle sensor includes one or more spectroscopy sensors, capacitive sensors, spectrometers (e.g., ion mobility spectrometers, mass spectrometers), chemiresistors, lasers, electrochemical sensors, biosensors, or any combination thereof. In response to detecting the presence of one or more predetermined substances of interest, each particle sensor is configured to generate a detection signal. A "detection signal," as used herein, includes a signal including data indicating the presence of a substance of interest in a portion of the environment 102. For example, a detection signal includes data identifying the substance of interest, data identifying the portion of the environment 102, data indicating a location of the portion of the environment 102, a timestamp, or any combination thereof. In embodiments, each particle sensor is further configured to detect a particle count or particle density of a detected substance of interest. In some embodiments, to detect the presence of one or more substances of interest, each particle sensor compares the particle count or particle density to a predetermined substance threshold value. A "substance threshold value," as used herein, includes one or more threshold particle counts or particle densities associated with a substance of interest. In response to the particle count or particle density of a substance of interest exceeding the predetermined substance threshold value, a chemical sensor is configured to generate a detection signal indicating, for example, the presence of the substance of interest in a portion of an environment 102 monitored by the personal air quality device 104 including the particle sensor.

In embodiments, personal air quality detection system 100 (e.g., API 110, personal air quality devices 104, or both) is configured to detect one or more substances of interest based on one or more personal metrics associated with a user of a personal air quality device 104. That is to say, personal air quality detection system 100 is configured to determine one or more substances of interest to monitor in a portion of an environment 102 based on one or more personal metrics. Such personal metrics include, for example, data identifying one or more conditions (e.g., allergies to substances of interest, illnesses, diagnoses, intolerances to substances of interest, sensitivities to substances of interest), measurements (e.g., $VO_2$ max, heartrate, heart rate recovery, historical measurements), identifying information (e.g., occupation, age, sex, gender), preferences (e.g., aversions to substances of interest, tolerances of substances of interest, power preferences for a personal air quality device 104, timing preferences for a personal air quality device 104), or any combination thereof of a user of a personal air quality device 104. According to embodiments, personal metrics are based on one or more selections of one or more users, inputs received from one or more users, determinations by air quality detection system 100 (e.g., API 110, personal air quality devices 104, or both), or any combination thereof.

For example, personal metrics are based on one or more inputs received from a user of a personal air quality device 104.

To determine one or more substances of interest based on personal metrics, personal air quality detection system 100 (e.g., API 110, personal air quality devices 104, or both) is configured to, for example, determine one or more substance threshold values based on one or more personal metrics, generate one or more notifications based on one or more personal metrics, or both. As an example, based on one or more allergies, conditions, intolerances, diagnoses, or any combination thereof identified in the personal metrics of a user, API 110, personal air quality device 104, or both is configured to determine a particle count, particle density, or both of one or more substances of interest that are harmful to the allergies, conditions, intolerances, diagnoses, or any combination thereof identified in the personal metrics. For example, API 110, personal air quality device 104, or both are configured to determine a particle count, particle density, or both of one or more substances of interest that trigger an allergy (e.g., cause an allergy attack) identified in the personal metrics, exacerbate a condition (e.g., asthma) identified in the personal metrics, or that would otherwise harm a user related to the personal metrics. After determining a particle count, particle density, or both of one or more substances of interest that are harmful to the allergies, conditions, intolerances, diagnoses, or any combination thereof identified in the personal metrics, API 110, personal air quality device 104, or both generate one or more substance threshold values equal to the determined particle counts, particle densities, or both of the substances of interest. In embodiments, API 110, personal air quality device 104, or both determine a particle count, particle density, or both of one or more substances of interest that are harmful to the allergies, conditions, intolerances, diagnoses, or any combination thereof identified in the personal metrics based on data (e.g., user data, user measurements, medical data) accessible by network 106, stored on a personal air quality device 104, stored in a database 108, or any combination thereof. As another example, API 110, personal air quality device 104, or both are configured to determine a harmful particle count, harmful particle density, or both of one or more substances of interest likely to be encountered by an occupation indicated in the personal metrics, routinely encountered by an occupation indicated in the personal metrics, or otherwise associated by an occupation indicated in the personal metrics. To this end, in some embodiments, API 110, personal air quality device 104, or both are configured to determine a harmful particle count, harmful particle density, or both of one or more substances of interest associated with a warehouse worker occupation. For example, API 110, personal air quality device 104, or both are configured to determine a harmful particle count, harmful particle density, or both of the substances of interest known to be in the warehouse where the warehouse worker works. After determining the harmful particle count, harmful particle density, or both of the substances of interests associated with the occupation indicated in the personal metrics, API 110, personal air quality device 104, or both generate one or more substance threshold value equal to the determined harmful particle counts and harmful particle densities.

In some embodiments API 110, personal air quality device 104, or both are configured to generate one or more notifications based on one or more substance threshold values determined from one or more personal metrics of a user of a personal air quality device 104. To this end, in response to a particle sensor of a personal air quality device 104 determining a particle count, particle density, or both of a substance of interest in a portion of an environment 102 is equal to or exceeds one or more substance threshold values determined from one or more personal metrics of a user of a personal air quality device 104, API 110, personal air quality device 104, or both are configured to generate one or more notifications. As an example, in some embodiments, in response to a particle sensor of a personal air quality device 104 determining a particle count, particle density, or both of a substance of interest in a portion of an environment 102 is equal to or exceeds one or more substance threshold values determined from one or more personal metrics of a user, the personal air quality device 104 including the particle sensor sends a detection signal indicating that a substance of interest has exceed one or more levels (e.g., particle counts, particle densities) as indicated by one or more substance threshold values determined from the personal metrics of a user. After receiving such a detection signal, API 110 is configured to generate notifications for a user based on one or more personal metrics. For example, API 110 is configured to generate a notification configured to display information based on one or more personal metrics. As another example, API 110 is configured to generate a notification configured to display a warning level based on one or more personal metrics (e.g., an allergy of a user). According to embodiments, API 110 is configured to generate one or more notifications each configured to display a mitigation action. To generate such notifications, API 110 is configured to generate one or more mitigation actions based on a detection signal, detected particle count, detected particle density, personal metrics, or any combination thereof. Such mitigation actions include, for example, instructions for mitigating the effects of a substance of interest associated with the substance threshold value that was exceeded. For example, a mitigation action includes instructions indicating a user to open a window, open an application, leave an area, use an inhaler, put on a mask (e.g., surgical mask, N-95 Mask, KN-95 mask), or any combination thereof, to name a few.

According to some embodiments, personal air quality detection system 100 (e.g., API 110, personal air quality devices 104, or both) is configured to update one or more substance threshold values based on one or more personal metrics. For example, personal air quality detection system 100 (e.g., API 110, personal air quality devices 104, or both) is configured to update one or more default substance threshold values based one or more personal metrics. As an example, personal air quality detection system 100 personal air quality detection system 100 (e.g., API 110, personal air quality devices 104, or both) is configured to update a default substance threshold value (e.g., a substance threshold value for pollen) based on an allergy of the user (e.g., based on a particle count, particle density, or both of a substance of interest that would trigger an allergy attack).

In embodiments, personal air quality detection system 100 (e.g., API 110, personal air quality devices 104, or both) is configured to update one or more substance threshold values based on a current location of the user. For example, personal air quality detection system 100 (e.g., API 110, personal air quality devices 104, or both) is configured to update a default substance threshold based on the type of environment (e.g., school, office building, residence, dormitory, warehouse, factory, laboratory, hospital, yard, outdoor area) that a user is currently in. To this end, personal air quality detection system 100 (e.g., API 110, personal air quality devices 104, or both) is configured to determine the location of a user based on, for example, GPS coordinates of a wearable device, input from a user, data from RFID tags, data from low-energy Bluetooth beacons, or any combination thereof.

According to embodiments, each personal air quality device 104 includes or is associated with one or more location profiles each identifying respective substance threshold values, personal metrics of a user, or both associated with a type of environment (e.g., school, office building, residence, dormitory, warehouse, factory, laboratory, hospital, yard, outdoor area) particular environment (user's home, user's workplace), or both. Such location profiles are stored, for example, on a personal air quality detection device 104, in a database 108, or both. Based on a current location, each personal air quality device 104 is configured to select one or more location profiles associated with the current location of the user. As an example, in response to a user inputting that a biohazard zone is being entered, a personal air quality device 104 is configured to select a location profile associated with biohazard zones (e.g., a type of zone) that identifies substance threshold values associated with the biohazard zone. As an additional example, based on GPS coordinates indicating the user is currently indoors (e.g., a type of environment), a personal air quality device 104 is configured to select a first location profile associated with indoor environments that identifies respective substance threshold values and personal metrics. Further, for example, based on GPS coordinates indicating the user is currently outdoors (e.g., a type of environment), the personal air quality device 104 is configured to select a second location profile associated with outdoor environments identifying respective substance threshold values and personal metrics. Additionally, after selecting a location profile, a personal air quality device 104 is configured to monitor a portion of an environment 102 based on the substance threshold values indicated in the location profile, determine substance threshold values based on the personal metrics indicated in the location profile, or both.

In embodiments, one or more personal air quality devices 104 are configured to monitor a portion of environment 102 in response to an activation event. In some embodiments, such an activation event includes, for example, a manual activation of a personal air quality device, a user input (e.g., gesture, key stroke, mouse drag, mouse click, tap) received at a personal air quality device, a personal air quality device entering a portion of a predetermined type of environment, or any combination thereof. According to other embodiments, an activation event includes, for example, one or more sensors of a sensor suite (e.g., particle sensor, chemical sensor, humidity sensor, temperature sensor) measuring values above or below a predetermined threshold value. As an example, an activation event includes a temperature sensor measuring a temperature of an environment 102 that exceeds a predetermined threshold value. As another example, an activation event includes a particle sensor measuring a particle count over a predetermined substance threshold value. In embodiments, a personal air quality device 104 is configured to determine an activation event to be monitored based on one or more personal metrics, a current location of a user, or both. That is to say, based on personal metrics, a current location of the user, or both, a personal air quality device 104 is configured to, for example, set one or more predetermined thresholds related to one or more sensors of a sensor suite for one or more activation events. For example, based on the occupation of a user being a firefighter, a predetermined threshold (e.g., temperature) is set for a temperature sensor. As another example, in response to a user entering an environment 102, a predetermined threshold (e.g., particle count for pollen) is set for a particle sensor. As yet another example, in response to the occupation of a user being a warehouse worker, a predetermined threshold (e.g., particle density of one or more gasses) is set for a particle sensor.

According to embodiments, a personal air quality device 104 is configured to monitor a portion of an environment in response to an activation signal when it is powered by, for example, a battery, a generator, or any combination of the two. In embodiments, one or more personal air quality devices 104 are configured to monitor a portion of an environment 102 of the user periodically, for example, at predetermined intervals of time including seconds, minutes, hours, days, weeks, months, or any combination thereof. In some embodiments, a personal air quality device 104 is configured to determine, update, or adjust the period for monitoring an environment 102 based on one or more personal metrics (e.g., user tolerance for a substance). For example, a personal air quality device 104 is configured to determine the period for monitoring a portion of an environment 102 according to a user tolerance for a substance of interest identified in a personal metric. Such a user tolerance includes, for example, data representing an acceptable level (e.g., none, low, moderate, high) for one or more substances. In embodiments, each acceptable level for a substance is associated with one or more predetermined values for particle density, particle count, or both. For example, based on a user tolerance indicating an acceptable level of low for pollen, a personal air quality device may increase the period for monitoring.

In embodiments, one or more personal air quality devices 104 are communicatively coupled to databases 108 and API 110 by network 106. "Communicatively coupled," as used herein includes the capability of transferring or receiving data using one or more communication protocols (e.g., TCP, UDP, POP, SMTP, IP, HTML, FTP, BACnet, BACnet Secure Connect, Modbus, Internet Technologies/Protocols, LonWorks, Common Industrial Protocol, Telnet, Bluetooth, Bluetooth LTE, Zigbee, or any combination thereof, to name a few). Network 106 includes one or more wired and wireless connections configured to communicatively couple personal air quality devices 104, database 108, and API 110 and includes, for example, the Internet, LAN, ad-hoc connections, Bluetooth, RFID, NFC, Ethernet, Intranet, Wi-Fi, cellular networks (e.g., 4G, 5G), Piconet, or any combination thereof. According to embodiments, air quality detection system 102 is configured to send one or more detections signals, detected particle counts, detected particle densities, or any combination thereof, from one or more personal air quality devices 104 to databases 108 and API 110 via network 106.

In embodiments, personal air quality detection system 100 is configured to store one or more received detection signals, detected particle counts, detected particle densities, or any combination thereof received from one or more personal air quality devices 104 in databases 108. Databases 108 include hardware and software configured to store and manage personal historical air quality data associated with one or more users, for example, one or more processing cores, microcontrollers, memories, or any combination thereof. Personal historical air quality data includes, for example, previously received detection signals, detected particle counts, detected particle densities, or any combination thereof associated with one or more users and stored in databases 108. According to embodiments, databases 108 are configured to associate each received detection signal, detected particle count, and detected particle density with data associated with their creation. Such data includes the time, location, substance of interest, and user (e.g., user credentials, user profile) associated with the creation of the detection signal, detected particle count, or detected particle density. In embodiments, air quality detection system 100 is configured to determine one or more substance threshold values (e.g., default substance threshold values, updated substance threshold values) for a personal air quality device associated with a user based on the personal historical air quality data associated with the user. For example, air quality system 100 is configured to perform one or more operations, filter, sort, or any combination thereof personal historical air quality data to determine one or more substance threshold values.

With continued reference to FIG. 1, personal air quality detection system 100 includes API 110. According to embodiments, API 110 is executed on one or more servers (e.g., virtual servers, cloud-based servers, or both each communicatively coupled to one another by network 106), personal air quality devices 104, or both. For example, one or more servers are configured to execute at least a portion of API 110 and one or more personal air quality devices 104 are configured to execute at least a different portion of API 110 such that data can be exchanged, processed, modified, stored, and recalled at and between the servers and personal air quality devices 104. In embodiments, in response to a personal air quality device 104 detecting that one or more substance threshold values are exceeded, API 110 is configured to generate one or more notifications. For example, in response to one or more received detection signals indicating a substance threshold value has been exceeded, API 110 is configured to generate a notification. Such notifications include, for example, displayable data indicating detected particles counts, detected substances, warning level (e.g., low, medium high), or any combination thereof associated with the substance threshold values being exceeded. According to embodiments, one or more notifications include prompts for the user to input information such personal metrics, an acknowledgement, a request for emergency services, or any combination thereof.

Figure 2:
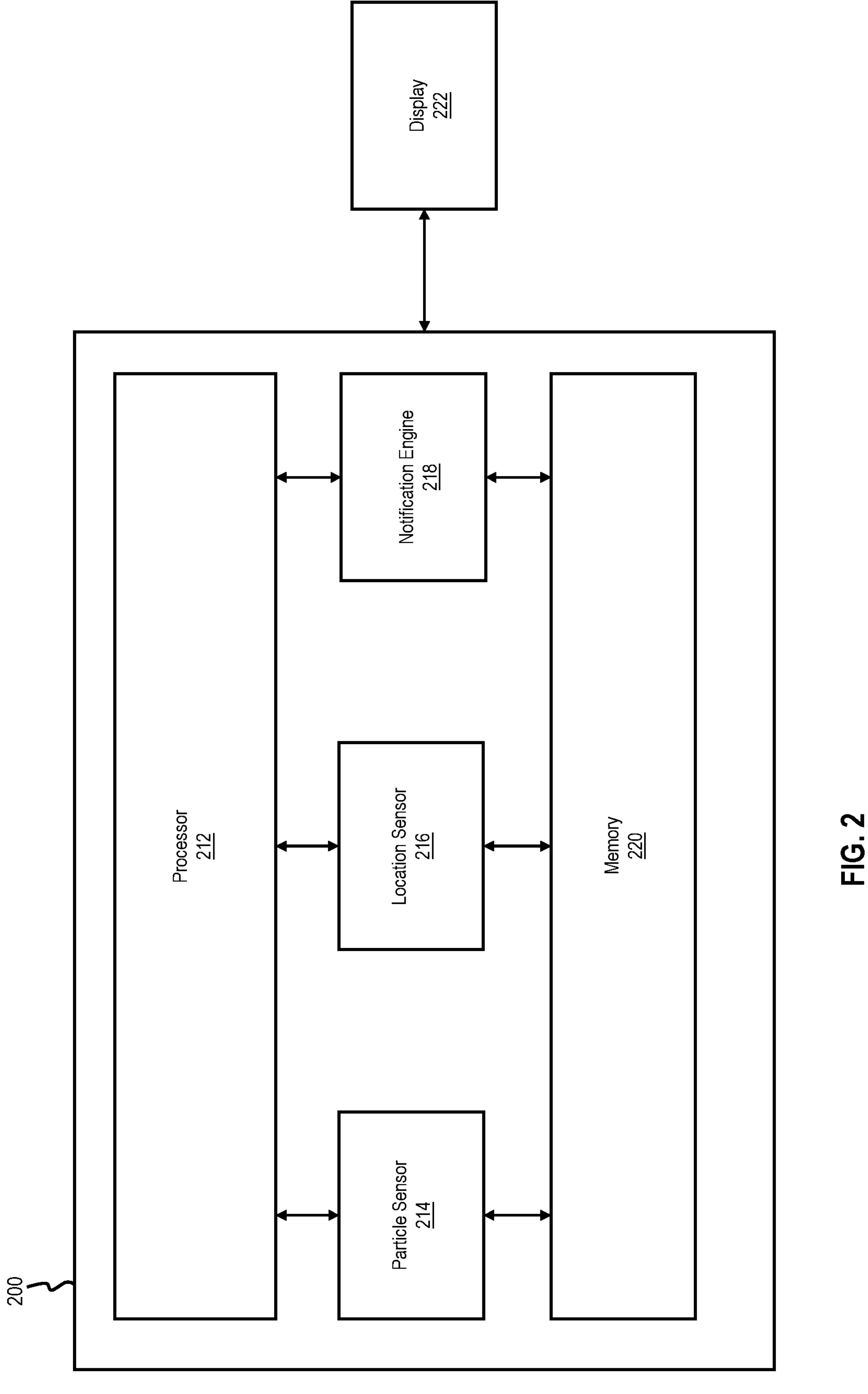
FIG. 2 illustrates a block diagram of a personal air quality detection device, according to embodiments.

Referring now to FIG. 2, a block diagram of a personal air quality detection device 200 is presented. In some embodiments, personal air quality detection device 200, similar to or the same as a personal air quality device 104, is partially or wholly encapsulated, embedded, or encased in a wearable technology device (e.g., smartwatch, fitness tracker, wearable sensor) while in other embodiments personal air quality detection device 200 comprises a wearable device. According to embodiments, personal air quality detection device 200 includes a processor 212 that includes hardware-based circuitry, software-based circuitry, or both configured to perform operations and execute instructions on behalf of the personal air quality detection device 200. For example, processor 212 includes one or more parallel processors, sequential processors, hardware accelerators, programmable memory devices (e.g., field-programmable gate arrays), central processing units (CPUs), graphics processing units (GPUs), microcontrollers, or any combination thereof configured to execute instructions for the personal air quality detection device 200. Further, personal air quality detection device 200 includes or is otherwise communicatively coupled to one or more displays 222. Such displays 222, for example, include one or more output devices such as screens disposed on a device (e.g., smartphones, tablets, computer devices, wearable devices, cellphones), earphones, headphones, heads-up displays, a projection, a hologram, or any combination thereof. In embodiments, display 222 includes integrated speakers and/or haptic output devices, such as devices capable of generating vibrations. Within personal air quality detection device 200, processor 212 is communicatively coupled to a memory 220. Such a memory 220 includes, for example, a non-volatile memory such as a read-only memory (ROM), programmable read-only memory (PROM), electronically erasable read-only memory (EEPROM), solid-state drive (SSD), hard-disk drive (HDD), flash memory, or any combination thereof. Additionally, or alternatively, memory 220 further includes a volatile memory such as dynamic random-access memory (DRAM), static random-access memory (SRAM), hardware caches, and the like.

In embodiments, processor 212 is configured to determine one or more substance threshold values based on one or more user profiles, personal metrics, or both of a user associated with the personal air quality detection device 200. Such user profiles, for example, includes data identifying one or more substances of interest to be measured (e.g., data identifying which substances of interest to monitor in a portion of an environment 102), one or more threshold values (e.g., substance threshold values) associated with one or more substances of interest, one or more personal metrics of a user, or any combination thereof. Personal metrics, for example, include one or more conditions (e.g., allergies to substances of interest, illnesses, diagnoses, intolerances to substances of interest, sensitivities to substances of interest), measurements (e.g., $VO_2$ max, heartrate, heart rate recovery, historical measurements), identifying information (e.g., occupation, age, sex, gender), preferences (e.g., aversions to substances of interest, tolerances of substances of interest, power preferences for a personal air quality device 104, timing preferences for a personal air quality device 104), or any combination thereof of a user of a personal air quality device 104. To determine one or more substances of interest based on personal metrics, processor 212 is configured to determine one or more substance threshold values based on one or more personal metrics. As an example, based on one or more allergies, conditions, intolerances, diagnoses, or any combination thereof identified in the personal metrics of a user, processor 212 is configured to determine a particle count, particle density, or both of one or more substances of interest that are harmful to the allergies, conditions, intolerances, diagnoses, or any combination thereof identified in the personal metrics. To this end, for example, processor 212 is configured to determine a particle count, particle density, or both of one or more substances of interest that trigger an allergy (e.g., cause an allergy attack) identified in the personal metrics, harmful to a condition (e.g., harmful to an immunocompromised condition) identified in the personal metrics, or that would otherwise harm a user related to the personal metrics. After determining a particle count, particle density, or both of one or more substances of interest that are harmful to the allergies, conditions, intolerances, diagnoses, or any combination thereof identified in the personal metrics processor 112 is configured to generate one or more substance threshold values equal to the determined particle counts, particle densities, or both of the substances of interest. As another example, processor 112 is configured to determine a harmful particle count, harmful particle density, or both of one or more substances of interest likely to be encountered by an occupation indicated in the personal metrics, routinely encountered by an occupation indicated in the personal metrics, or otherwise associated by an occupation indicated in the personal metrics. To this end, in some embodiments, processor 112 is configured to determine a harmful particle count, harmful particle density, or both of one or more substances of interest associated with a lab technician. For example, processor 112 is configured to determine a harmful particle count, harmful particle density, or both of the substances of interest known to be in a lab where the lab technician works. After determining the harmful particle count, harmful particle density, or both of the substances of interests associated with the occupation indicated in the personal metrics, processor 112 generates one or more substance threshold values equal to the determined harmful particle counts and harmful particle densities.

To monitor the air quality of an environment based on one or more determined substance threshold values, personal air quality detection device 200 includes a particle sensor 214 that includes hardware-based circuitry, software-based circuitry, or both configured to measure the particle count, particle density, or both of one or more substances of interest in at least a portion of an environment 102. According to embodiments, particle sensor 214 is the same as or similar to personal air quality devices 104, sensor suites, detection units, or any combination thereof as described herein. In embodiments, particle sensor 214 includes a plurality of sensors each including hardware-based circuitry, software-based circuitry, or both configured to detect particle counts, particle densities, or both of one or more substances of interest.

In embodiments, particle counts, particle densities, or both monitored by particle sensor 214 are provided to processor 212. Based on the measured particle counts, particle densities, or both, processor 212 is configured to generate one or more detection signals based on the one or more as disclosed in U.S. Pat. No. 11,195,406 or U.S. Pat. No. 11,030,877. For example, in response to a measured particle count, particle density, or both of a substance of interest being equal to or exceeding a substance threshold value, processor 112 is configured to generate a detection signal indicating, for example, the substance of interest that was detected, the measured particle count, the measured particle density, the location in an environment 102 in which the substance of interest was detected, the user associated with the personal air quality device 200, or any combination thereof. Further, in some embodiments, processor 112 is configured to send such a detection signal to API 110 via network 106.

In embodiments, personal air quality detection device 200 includes a location sensor 216. Location sensor 216 includes hardware and/or software configured to determine a location of personal air quality detection device 200. For example, location sensor 216 includes hardware-based circuitry, software-based circuitry, or both configured to track a location of personal air quality device 200 according to GPS signals, light gate signals, proximity sensor signals, radio frequency identification (RFID) signals, near-field communication (NFC) signals, video, Bluetooth signals, WI-FI signals, or any combination thereof. According to embodiments, location sensor 216 is configured to determine if air quality detection device 200 enters one or more types of environments (e.g., office building, school, biohazard area). For example, location sensor 216 is configured to compare one or more GPS signals, light gate signals, proximity sensor signals, NFC signals, RFID signals, video, Bluetooth signals, or WI-FI signals to one or more values stored in memory 220 to determine a location of the personal air quality detection device 200 and the type of environment of the location. According to embodiments, in response to air quality detection device 200 entering one or more types of an environment, processor 212 is configured to activate particle sensor 214. For example, processor 212 is configured to provide power to particle sensor 214, issue a command to particle sensor 214, execute one or more applications, or any combination thereof in response to air quality detection device 200 entering one or more types of an environment.

Personal air quality detection device 200 further includes notification engine 218 including hardware-based circuitry, software-based circuitry, or both configured to generate one or more notifications based on one or more received detection signals, detected particle counts, detected particle densities, personal metrics, or any combination thereof. For example, in response to particle sensor 214 generating a detection signal, notification engine 218 is configured to generate one or more notifications based one or more personal metrics. Such notifications include displayable data indicating detected particles counts, detected substances, warning level (e.g., low, medium high), or any combination thereof associated with the substance threshold values being exceeded. In embodiments, notifications generated by notification engine 218 are output by personal air quality detection device 200, displayed on display 222, transmitted to another system via network 106, or any combination thereof. According to embodiments, one or more notifications include prompts for the user to input information such personal metrics, an acknowledgement, a request for emergency services, or any combination thereof. In embodiments, notification engine 218 is configured to generate notifications to a user based on one or more personal metrics. As another example, notification engine 218 is configured to generate a notification configured to display a warning level based on one or more personal metrics (e.g., an allergy of a user). According to embodiments, notification engine 218 is configured to generate one or more notifications each configured to display a mitigation action. To generate such notifications, notification engine 218 is configured to generate one or more mitigation actions based on one or more detection signals, particle counts, particle densities, personal metrics, or any combination thereof. For example, notification engine 218 is configured to generate a notification including a prompt for a user to open a window, leave an environment, or put on a mask.

Figure 3:
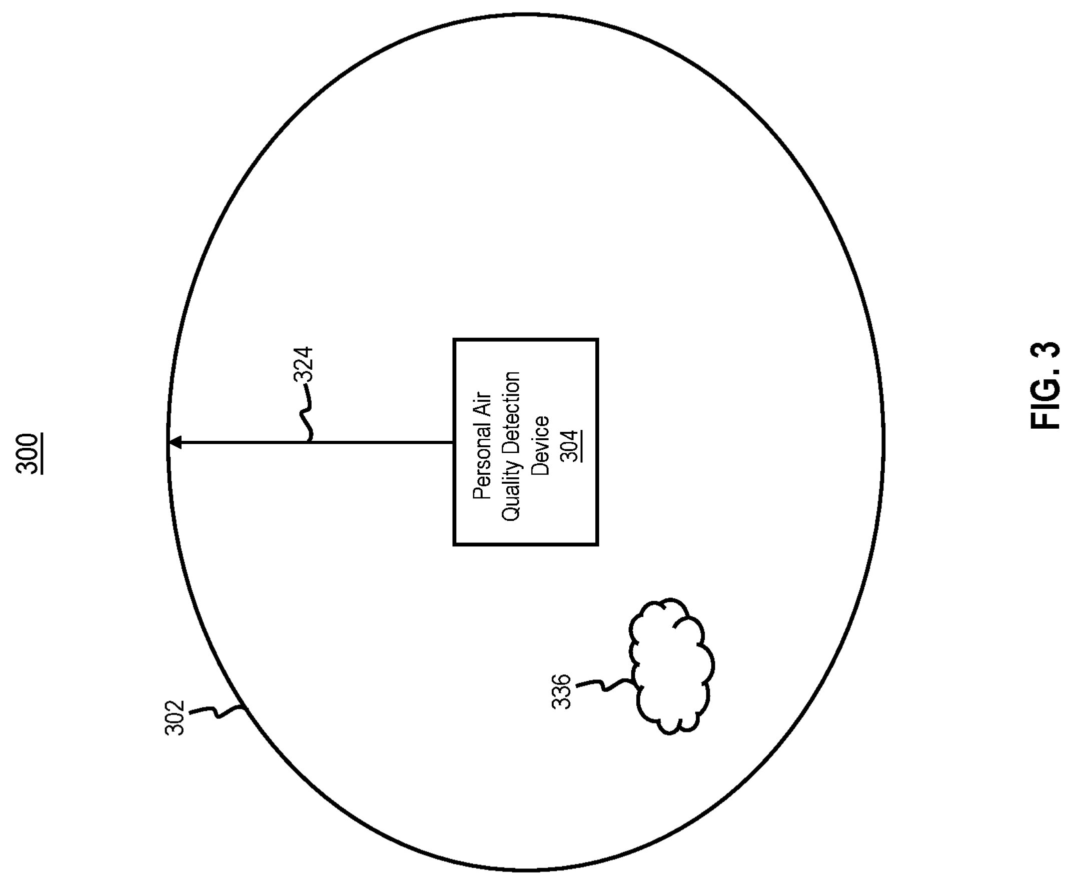
FIG. 3 illustrates a block diagram of a personal air quality detection device for monitoring a first portion of an environment, according to embodiments.

Referring now to FIG. 3, a personal air quality detection system 300 in a portion of an environment 302 is presented. The portion of an environment 302, similar to or the same as environment 102, includes, for example, a dining hall, an office, a dorm, a conference room, a courtyard, a bedroom, a laboratory, or a warehouse, to name a few. Air quality detection system 300 includes personal air quality device 304, similar to or the same as personal air quality device 104, 200. In embodiments, personal air quality device 304 is configured to monitor a portion of environment 302 for the presence of a substance of interest 336. Such a substance of interest 336 includes, for example, one or more airborne gasses, and/or particles that are to be monitored in at least a portion of the environment 302. As an example, substance of interest 336 includes one or more substances that are illegal, prohibited, or discouraged for one or more users within environment 302 such as emissions from a vaporization device (e.g., nicotine vaping device, cannabinoid vaping device, tetrahydrocannabinol vaping device), emissions from nicotine products (e.g., cigarettes, cigars, pipes), emissions from illegal, prohibited, or discouraged drugs (e.g., methamphetamine, fentanyl), or any combination thereof. Further, in some embodiments, substance of interest 336 includes one or more substances that are hazardous to one or more users within environment 302, one or more user associated with one or more personal air quality devices 104, 200, or both. Such hazardous substances include, for example, hazardous gasses (e.g., arsine, dimethyl sulfate, toluene, hydrogen azide, hydrogen cyanide, nitrogen dioxide, ammonia), biological substances (e.g., viruses, bacteria, fungus, pollen, dust, mold), or any combination thereof. As another example, substance of interest 336 includes substances not tolerated by one or more users associated with one or more personal air quality detection devices 104, 200 such as, but not limited to, animal odors (e.g., animal urine, animal feces, animal sweat), chemical odors (e.g., perfumes, colognes, body sprays), food odors, or any combination thereof. In embodiments, substance of interest 336 includes aerosolized particles, droplets, gasses, or any combination thereof.

According to some embodiments, personal air quality device 304 is configured to monitor a portion of environment 302 based on a location radius 324. The location radius 324 includes a radial distance away from personal air quality device 304 that is monitored for substances of interest 336. That is to say, location radius 324 represents the distance within which personal air quality detection device 304 monitors air quality. In embodiments, personal air quality detection system 300 is configured to modify location radius 324 based on personal metrics, detection signals, or both. As an example, in response to personal air quality detection device 304 (e.g., a processor 212 of the personal air quality detection device 304) determining that a particle count, particle density or both of substance of interest 334 is equal to or exceeds a substance threshold value, personal air quality detection device 304 increases location radius 324 such that personal air quality detection device 304 monitors for substance of interest 336, one or more other substances of interest, or both within the increased location radius 324. As another example, based on a personal metric indicating an allergy to substance of interest 334, personal air quality device 304 is configured to increase location radius 324 such that personal air quality detection device 304 monitors for substance of interest 336 within the increased location radius 324. As yet another example, in response to a personal metric indicating a high tolerance for substance of interest 336, location radius 324 is reduced such that personal air quality detection device 304 monitors for substance of interest 336 within the decreased location radius 324. Likewise, in response to a personal metric indicating low tolerance or no tolerance for substance of interest 336, location radius 324 is increased such that personal air quality detection device 304 monitors for substance of interest 336 within the increased location radius 324.

Additionally, in some embodiments, personal air quality detection device 304 is configured to modify location radius 324 based on a location of the personal air quality detection device 304. To this end, in embodiments, personal air quality detection device 304 is configured to determined one or more locations based one or more personal metrics. As an example, personal air quality detection device is configured to determine a home location of a user from one or more personal metrics (e.g., an address of the user), a workplace of the user based on one or more personal metrics (e.g., occupation of a user), or both. In response to personal air quality detection device 304 (e.g., a location sensor 216 of the personal air quality detection device 304) determining that the personal air quality detection device 304 has entered one or more determined locations, personal air quality detection device 304 increases location radius 324, decreases location radius 324, or both. As an example, in response to determining the personal air quality detection device 304 has entered a workplace of the user, personal air quality detection device 304 increases location radius 324 such that personal air quality detection device 304 monitors for substance of interest 336 within the increased location radius 324. As another example, in response to determining the personal air quality detection device 304 has entered a home of the user, personal air quality detection device 304 decreases location radius 324 such that personal air quality detection device 304 monitors for substance of interest 336 within the decreased location radius 324

Figure 4:
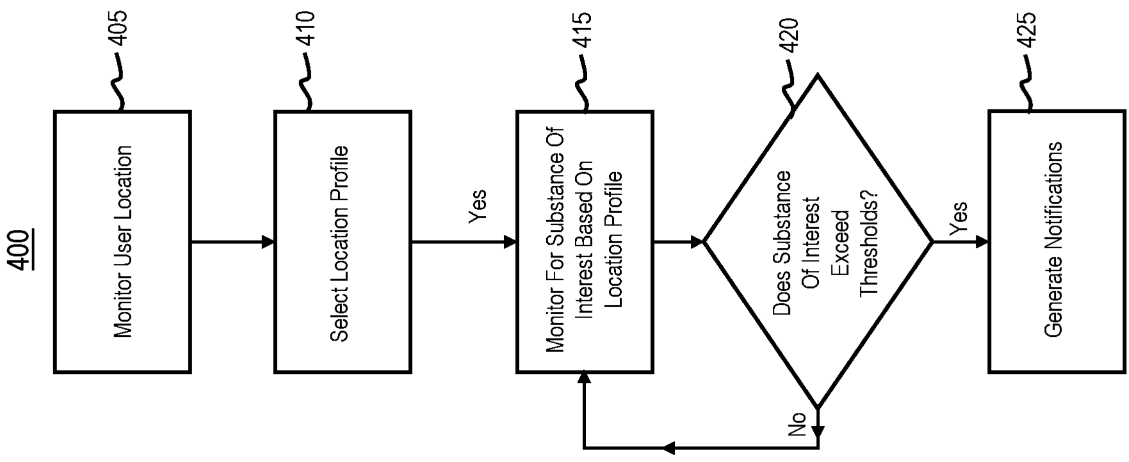
FIG. 4 illustrates a flow diagram of an example method for monitoring and reporting personal air quality data for a user, according to embodiments.

Referring now to FIG. 4, an example method 400 for personal air quality detection and notification is presented. At step 405, a personal air quality detection device, similar to or the same as personal air quality detection device 104, 200, 304, monitors the location of a user. That is to say, the personal air quality detection device determines a type of environment (e.g., school, office building, residence, dormitory, warehouse, factory, laboratory, hospital, yard, outdoor area) particular environment (user's home, user's workplace), or both that a user is currently in. For example, the personal air quality detection device sensor determines that a user is outside (e.g., a type of environment) based on a GPS signal. As another example, the personal air quality detection device determines that the user is at the user's place of work based on one or more RFID signals received by the personal air quality detection device and one or more personal metrics associated with the personal air quality detection device. As yet another example, the personal air quality detection devices determines that a user has entered a biohazard area (e.g., a type of environment) based on one or more NFC signals received by the personal air quality detection device.

At step 410, the personal air quality detection device determines a location profile associated with the determined location. That is to say the personal air quality detection device determines a location profile associated with the type of environment, particular environment, or both that the user is determined to be in. For example, in response to determining the user has entered an indoor environment (e.g., a type of environment) the personal air quality detection device selects a location profile identifying one or more substance threshold values related to one or more substances of interest. At step 415, the personal air quality detection device monitors for one or more substances of interest based on the selected location profile. For example, the personal air quality detection device monitors for one or more substances of interest based on one or more substance threshold values identified in a selected location profile. Further, in some embodiments, personal air quality detection device monitors for one or more substances of interest within location radius 324. In embodiments, based on the determined location of the user, the personal air quality detection device is configured to modify location radius 324. For example, based on the type of environment, particular environment, or both that the user is determined to be in, the personal air quality detection device increases or decreases location radius 324. As an example, in response to determining that a user has entered an outdoor environment (a type of environment), the personal air quality detection device decreases location radius 324. As another example, in response to determining that the user has entered the user's place of work, the personal air detection device increases location radius 324.

At step 420, the personal air quality device determines if a detection event has occurred based on the selected location profiled. That is to say, the personal air quality device determines one or more monitored particle densities, particle counts, or both of one or more predetermined substances of interest exceed one or more user substance threshold value indicated in the selected location profile within the modified location radius 324. In response to one or more monitored particle densities, particle counts, or both of one or more predetermined substances of interest exceeding one or more substance value thresholds, the system moves to step 425. In response to one or more monitored particle densities, particle counts, or both of one or more predetermined substances of interest not exceeding one or more substance threshold values, the system repeats step 415. At step 425, the personal air detection device generates one or more notifications. A notification includes, for example, displayable data indicating a portion of the environment, substance of interest, particle count, particle density, or any combination thereof, associated with one or more received detection signals. In embodiments, the personal air quality detection device is configured to output one or more generated notifications. For example, the personal air quality detection device displays one or more generated notifications.

Figure 5:
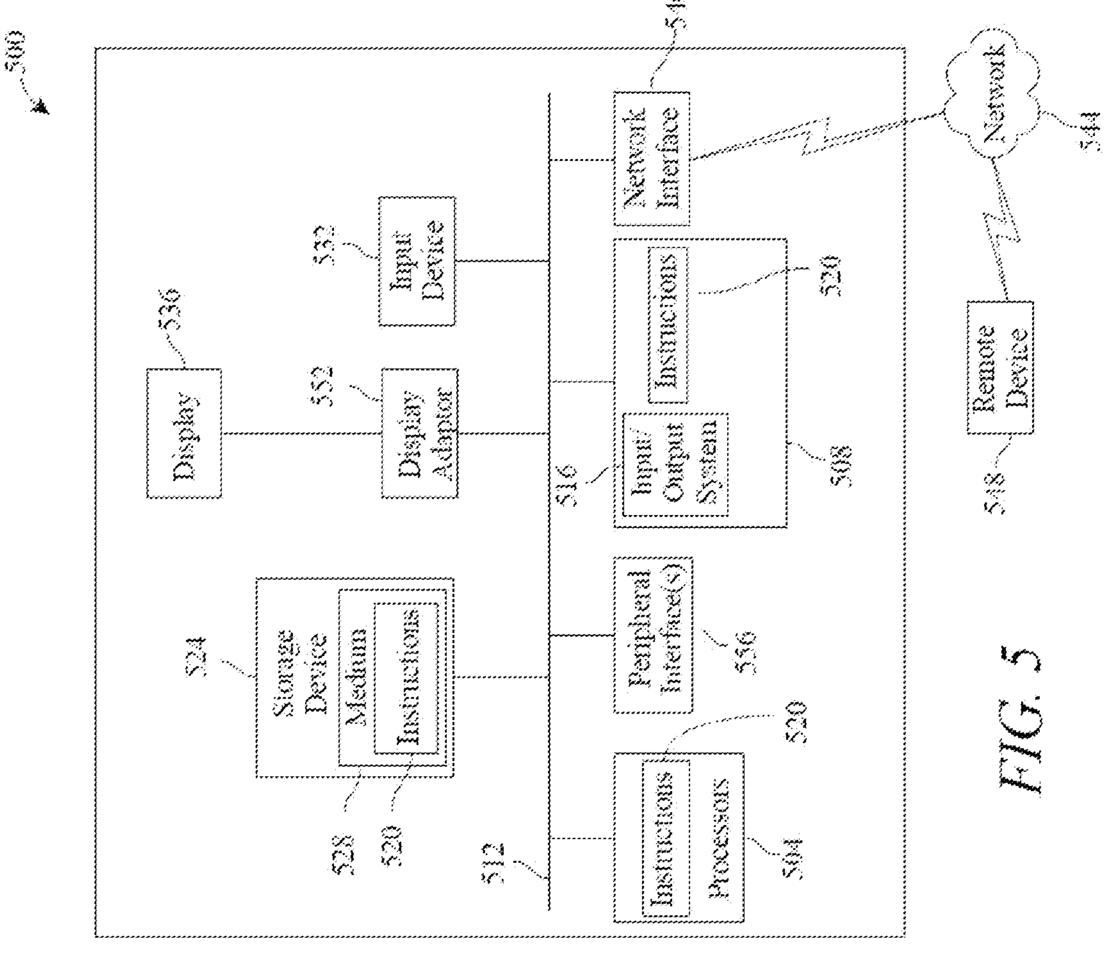
FIG. 5 illustrates a block diagram of an example computing device in the example form of a computer system, according to embodiments.

FIG. 5 shows a diagrammatic representation of one embodiment of a computing device in the exemplary form of a computer system 500 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 500 includes a processor 504 and a memory 508 that communicate with each other, and with other components, via a bus 512. Bus 512 may include any of several types of bus structures including, but not limited to, a memory bus, a memory controller, a peripheral bus, a local bus, and any combinations thereof, using any of a variety of bus architectures.

Processor 504 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 504 may be organized according to Von Neumann and/or Harvard architecture as a non-limiting example. Processor 504 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC).

Memory 508 may include various components (e.g., machine-readable media) including, but not limited to, a random-access memory component, a read-only component, and any combinations thereof. In one example, a basic input/output system 516 (BIOS), including basic routines that help to transfer information between elements within computer system 500, such as during start-up, may be stored in memory 508. Memory 508 may also include (e.g., stored on one or more machine-readable media) instructions (e.g., software) 520 embodying any one or more of the aspects and/or methodologies of the present disclosure. In another example, memory 508 may further include any number of program modules including, but not limited to, an operating system, one or more application programs, other program modules, program data, and any combinations thereof.

Computer system 500 may also include a storage device 524. Examples of a storage device (e.g., storage device 524) include, but are not limited to, a hard disk drive, a magnetic disk drive, an optical disc drive in combination with an optical medium, a solid-state memory device, and any combinations thereof. Storage device 524 may be connected to bus 512 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 524 (or one or more components thereof) may be removably interfaced with computer system 500 (e.g., via an external port connector (not shown)). Particularly, storage device 524 and an associated machine-readable medium 528 may provide nonvolatile and/or volatile storage of machine-readable instructions, data structures, program modules, and/or other data for computer system 500. In one example, software 520 may reside, completely or partially, within machine-readable medium 528. In another example, software 520 may reside, completely or partially, within processor 504.

Computer system 500 may also include an input device 532. In one example, a user of computer system 500 may enter commands and/or other information into the computer system via input device 532. Examples of an input device 532 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device, a touchscreen, and any combinations thereof. Input device 532 may be interfaced to bus 512 via any of a variety of interfaces (not shown) including, but not limited to, a serial interface, a parallel interface, a game port, a USB interface, a FIREWIRE interface, a direct interface to bus 512, and any combinations thereof. Input device 532 may include a touch screen interface that may be a part of or separate from display 536, discussed further below. Input device 532 may be utilized as a user selection device for selecting one or more graphical representations in a graphical interface as described above.

A user may also input commands and/or other information to computer system 500 via storage device 524 (e.g., a removable disk drive, a flash drive, etc.) and/or network interface device 540. A network interface device, such as network interface device 540, may be utilized for connecting computer system 500 to one or more of a variety of networks, such as network 544, and one or more remote devices 548 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 544, may employ a wired and/or a wireless mode of communication. In general, any network topology may be used. Information (e.g., data, software 520, etc.) may be communicated to and/or from computer system 500 via network interface device 540.

Computer system 500 may further include a video display adapter 552 for communicating a displayable image to a display device, such as display device 536. Examples of a display device include, but are not limited to, a liquid crystal display (LCD), a cathode ray tube (CRT), a plasma display, a light emitting diode (LED) display, and any combinations thereof. Display adapter 552 and display device 536 may be utilized in combination with processor 504 to provide graphical representations of aspects of the present disclosure. In addition to a display device, computer system 500 may include one or more other peripheral output devices including, but not limited to, an audio speaker, a printer, and any combinations thereof. Such peripheral output devices may be connected to bus 512 via a peripheral interface 556. Examples of a peripheral interface include, but are not limited to, a serial port, a USB connection, a FIREWIRE connection, a parallel connection, and any combinations thereof.

Figure 6:
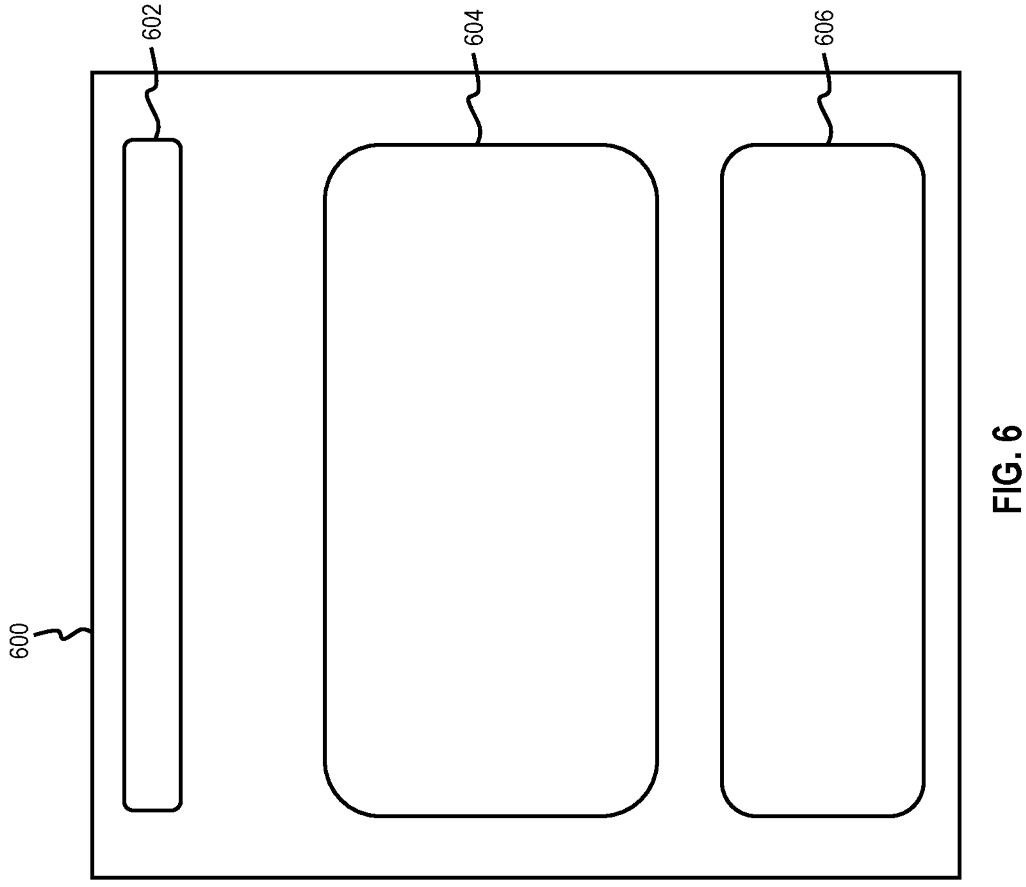
FIG. 6 illustrates a block diagram of an example graphical user interface configured to display and input information, according to embodiments.

Referring now to FIG. 6, an example graphical user interface (GUI) 600 configured to display and input information is presented. In embodiments, GUI 600 is displayable on one or more displays, similar to or the same as display 222. For example, GUI 600 is displayable on a smartphone, a wearable device, a computer screen, a heads-up display, a touch screen, a combination thereof, to name a few examples. GUI 600 includes notifications 602, 604 generated, for example, by a personal air quality detection device 104, 200, 304, API 110, or both. Notifications 602, 604 each includes, for example, one or more elements of interactive data related to air quality such as the time, location, or both of one or more monitored particle densities, particle counts, or both, exceeding one or more substance threshold values. According to embodiments, notifications 602, 604 each includes data associated with a push notification, phone call, text message, email, data readout, siren, textual prompt, visual notification, audio notification, haptic notification, or any combination thereof.

Still referring to FIG. 6, GUI 600 includes a second notification 604. Second notification 604 includes any of the information described with reference to push notification 602 or notifications in general herein.

With continued reference to FIG. 6, GUI 600 includes an input window 606. In embodiments, input window 606 includes one or more prompts indicating to a user to input data related to personal air quality devices, user credentials (e.g., user ID, password), personal metrics, location, or any combination thereof. Input window 606 is configured to receive one or more inputs as one or more interactions with GUI 600. Such interactions include, for example, a click, press, hold, switch, gesture, or any combination thereof within GUI 600.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A method for air quality detection, the method comprising:

in response to a personal air quality detection device entering a location, selecting a location profile associated with the location from a set of location profiles stored at the personal air quality detection device, the location profile identifying a substance threshold value;

comparing, by the personal air quality detection device, a substance of interest to the substance threshold value; and based on the comparison, displaying one or more notifications associated with the substance of interest.

2. The method of claim 1, further comprising:

modifying a location radius of the personal air quality detection device in response to the personal air quality detection device entering the location; and monitoring the location for the substance of interest within the modified location radius.

3. The method of claim 1, further comprising:

in response to the personal air quality detection device entering the location, modifying a location radius of the personal air quality detection device based on a personal metric stored at the personal air quality detection device and associated with a user of the personal air quality detection device, the personal metric indicating a user tolerance for the substance of interest; and monitoring the location for the substance of interest within the modified location radius.

4. The method of claim 1, further comprising:

in response to the personal air quality detection device entering the location, modifying the substance threshold value based on a personal metric associated with the personal air quality detection device, the personal metric indicating a user tolerance for the substance of interest.

5. The method of claim 1, wherein the personal air quality detection device includes a wearable device.

6. The method of claim 1, further comprising:

in response to entering the location, activating a particle sensor of the personal air quality detection device.

7. A method for air quality detection, the method comprising:

in response to a personal air quality detection device entering a location, modifying a location radius associated with the personal air quality detection device based on a personal metric stored at the personal air quality detection device, the personal metric indicating a user tolerance for a substance of interest;

monitoring the substance of interest within the modified location radius; and in response to the substance of interest exceeding a substance threshold value, displaying one or more notifications associated with the substance of interest.

8. The method of claim 7, further comprising:

determining the substance threshold value based on the user tolerance for the substance of interest.

9. The method of claim 7, further comprising:

determining the substance threshold value based on the location of the personal air quality detection device.

10. The method of claim 7, further comprising:

modifying the location radius of the personal air quality detection device further based on a location profile associated with the location, the location profile included in a set of location profiles stored on the personal air quality detection device.

11. The method of claim 7, wherein the personal air quality detection device includes a wearable device.

12. The method of claim 7 further comprising:

in response to entering the location, activating a particle sensor of the personal air quality detection device.

13. A personal air quality detection device, comprising:

a memory storing a set of location profiles; and a processor configured to:

in response to the personal air quality detection device entering a location, select a location profile associated with the location from the set of location profiles, the location profile identifying a substance threshold value;

compare a substance of interest to the substance threshold value; and based on the comparison, display one or more notifications associated with the substance of interest.

14. The personal air quality detection device of claim 13, the processor configured to:

in response to the personal air quality detection device entering the location, modify a location radius of the personal air quality detection device based on the location profile.

15. The personal air quality detection device of claim 13, the processor configured to:

in response to the personal air quality detection device entering the location, modify a location radius of the personal air quality detection device based on a personal metric stored in the memory, the personal metric indicating a user tolerance for the substance of interest.

16. The personal air quality detection device of claim 13, the processor configured to:

in response to the personal air quality detection device entering the location, modify the substance threshold value based on a personal metric associated with the personal air quality detection device, the personal metric indicating a user tolerance for the substance of interest.

17. The personal air quality detection device of claim 13, further comprising a wearable device.

18. The personal air quality detection device of claim 13, the processor configured to:

in response to the personal air quality detection device entering the location, activate a particle sensor of the personal air quality detection device.

* * * * *